United States Patent [19]

Cousse et al.

[11] 4,122,199
[45] Oct. 24, 1978

[54] AMIDES OF PYRROLIDINOETHYLAMINE WHICH CAN BE USED IN TREATMENT OF COUGHS

[75] Inventors: Henri Cousse; Bernard Bonnaud; Jean-Pierre Tarayre; Silvano Casadio, all of Castres, France

[73] Assignee: Pierre Fabre S.A., France

[21] Appl. No.: 714,764

[22] Filed: Aug. 16, 1976

[30] Foreign Application Priority Data

Apr. 9, 1976 [FR] France ............................. 76 10754

[51] Int. Cl.² ............................................. A61K 31/40
[52] U.S. Cl. .................................... 424/274; 424/247; 424/267; 542/421; 544/39; 260/293.71; 260/326.33; 260/326.34; 260/326.43
[58] Field of Search ......... 260/326.47, 243 A, 326.43; 424/274

[56] References Cited

U.S. PATENT DOCUMENTS

| | | | |
|---|---|---|---|
| 2,627,517 | 2/1953 | Cusic | 260/243 A |
| 2,634,274 | 4/1953 | Krimmel | 260/326.43 |
| 2,862,965 | 12/1958 | Lott et al. | 260/326.43 |
| 2,932,645 | 4/1960 | Taylor et al. | 260/326.43 |
| 3,074,939 | 1/1963 | Davis | 260/243 A |
| 3,455,940 | 7/1969 | Stecker | 260/326.47 |

FOREIGN PATENT DOCUMENTS

| | | | |
|---|---|---|---|
| 1,017,761 | 10/1952 | France | 260/326.43 |
| 1,159,176 | 2/1958 | France | 260/326.43 |
| 1,230,431 | 4/1960 | France | 260/326.43 |

OTHER PUBLICATIONS

Weitzel et al, Chemical Abstracts, vol. 61, col. 4864b (1964) (abst. of Weitzel et al, Z. Physiol. Chem. vol. 336 pp. 107-126 (1964).

Primary Examiner—Henry R. Jiles
Assistant Examiner—R. W. Ramsuer
Attorney, Agent, or Firm—Gordon W. Hueschen

[57] ABSTRACT

New chemical compounds, which are pyrrolidinoethylamine amides, in the form of free bases and salts thereof, which are useful as antitussives, pharmaceutical compositions thereof, and method of treating therewith.

In the form of their salts, the compounds have the formula:

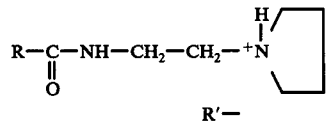

wherein

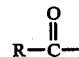

is an acyl radical of a phenylacetic, 60 -phenyl-α-(1 to 5 C atoms) acetic, (1 to 5 C atoms) diphenylacetic, benzilic, diphenyl-α-chloroacetic, α-lower-alkoxy-α,α-diphenylacetic, 3-coumarincarboxylic, 9-xanthenecarboxylic, phenoxyacetic, phenoxyisobutyric, halophenoxyisobutyric, or 9-flourene carboxylic acid, and wherein R'H represents an inorganic or organic acid.

Medicaments containing these active principles may be used, inter alia, in the treatment of coughs and respiratory complaints.

17 Claims, No Drawings

AMIDES OF PYRROLIDINOETHYLAMINE WHICH CAN BE USED IN TREATMENT OF COUGHS

BACKGROUND OF INVENTION (1) Field of Invention

New chemical compounds, pyrrolidinoethylamine amides, antitussives, compositions thereof, method of treating therewith.

(2) Prior Art

Much research work has been carried out in the search for nonmorphine derivatives which have antitussive properties. In this field, many structures have been studied and numerous patents and publications exist covering terpene molecules, dialkylamino-alkoxyethanol esters, and piperazine and piperidine derivatives. Numerous of these have been published during the last few years. On the other hand, few patents or articles mention pyrrolidine derivatives, especially of the type presently concerned, although new and useful antitussives, especially of a nonaddicting nature, would surely still be highly desirable.

SUMMARY OF THE INVENTION

The present invention relates to certain new chemical compounds, which are pyrrolidinoethylamine amides, in the form of free bases and salts thereof, which are useful as antitussives, pharmaceutical compositions thereof, and method of treating therewith.

In the form of their salts, the compounds have the formula:

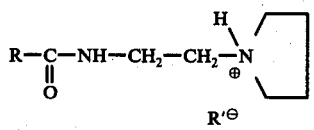

I wherein

is an acyl radical of a phenylacetic, α-phenyl-α-loweralkyl (1 to 5 C atoms) acetic, diphenylacetic, diphenyl-α-chloroacetic, benzilic, α-lower-alkoxy-α,α-diphenylacetic, 3-coumarincarboxylic, 9-xanthenecarboxylic, phenoxyacetic, phenoxyisobutyric, halophenoxyisobutyric, or 9-fluorene carboxylic acid, and wherein R'H represents an inorganic or organic acid

OBJECTS

It is accordingly an object of the present invention to provide certain novel pyrrolidinoethylamine amides, acid addition salts thereof, pharmaceutical compositions of the same in the form of either the free base or an acid addition salt thereof, and a method of treating therewith, especially a method of treating or ameliorating cough therewith. Another object is the provision of novel antitussive agents, compositions thereof, and method of treating therewith. Still other objects will become apparent hereinafter and additional objects will be obvious to one skilled in the art.

THE INVENTION

The invention, then, comprises (a) pyrrolidinoethylamine amides of the formula:

IA wherein RCO is as previously defined, and (b) acid addition salts therof. R is preferably a 9-xanthenyl, diphenyl—CH—, diphenyl—C(OH)—, or phenyl—CH($C_2H_5$)— radical, being derived respectively from 9-xanthenecarboxylic, diphenylacetic, diphenylhydroxyacetic, and alphaphenyl-alpha-ethylacetic acids. The acid addition salt may be of any of the usual types of acid, organic or inorganic, but from the standpoint of improved lipid solubility and flavor is preferably of the lipophilic type, e.g., a fatty acid of 14-22 carbon atoms, inclusive, e.g., palmitic, linoleic, linolenic, or oleic, or of the naphthoic type, especially pamoic, particularly when R has one of the preferred meanings assigned in the foregoing. When R has formula II as previously assigned, then $R_2$ is preferably allyloxy, hydroxy, or carboxy, $R_1$ is preferably methyl or hydrogen, and X is preferably bromine or hydrogen, or all three are methoxy.

These new chemical compounds forming an object of the invention can be obtained by the following methods, as illustrated by the following examples:

1st method

The acid chloride $$R-\overset{O}{\underset{\|}{C}}-Cl$$

is reacted with the pyrrolidinoethylamine in an organic solvent, for instance benzene or acetone.

2nd method

The pyrrolidinoethylamine is heated in the presence of a loweralkyl ester, for insance $$R-\overset{O}{\underset{\|}{C}}-OC_2H_5;$$

sodium is used as catalyst.

For sake of convenience, the compounds are at times designated by their code number.

DETAILED DESCRIPTION OF THE INVENTION

The following Examples are given by way of illustration only and are not to be construed as limiting.

EXAMPLE 1 (illustrates method 2)

Synthesis of N(2'-pyrrolidino-ethyl)-9-fluoroene-carboxamide hydrochloride (F 1532)

One mol (238 g) of ethyl 9-fluorene carboxylate is treated with 1.6 mol of 2-amino-ethyl pyrrolidine. Heated for 2 hours at 150° C., the ethanol distills over as it is formed. The reaction mass obtained is dissolved in methylene chloride, washed three times with water, dried, filtered, and distilled to dryness.

The base is then hydrochlorided in solution in a mixture of ethanol and methylene chloride.

The hydrochloride is precipitated by the addition of ether. The yield of hydrochloride (F 1532) referred to the ethyl ester is 85%.

Developed Formula

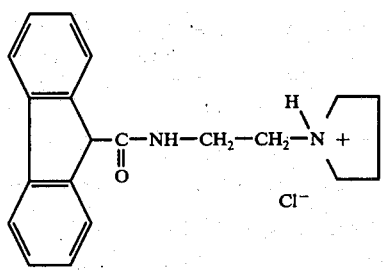

Empirical formula: $C_{20}H_{23}ClN_2O$
Molecular weight: 342.9
White crystals
Melting point: 198° C.

Plate chromatography: support: silica Merck G 254, solvent: butanol/acetic acid/water 6/2/2, development: ultraviolet lamp or iodine vapors, Rf: 0.64

Infrared spectrography: absorption band $\nu_{C=O}$ amide at 1675 cm$^{-1}$ $\nu_{C=C}$ aromatic at 1610 cm$^{-1}$ $\nu_{C-H}$ aromatic at 3070 cm$^{-1}$ Solubility characteristics: very soluble in water, ethanol and propylene glycol.

EXAMPLE 2 (illustrates the 1st method)

N(2'-pyrrolidino-ethyl)-9-xanthene carboxamide hydrochloride (F 1534)

The chloride of 9-xanthene carboxylic acid is obtained by treating 1 mol of acid, suspended in benzene, with thionyl chloride and then distilling to dryness. The crude acid chloride, dissolved in ether, is treated with a stoichiometric amount of N-2-pyrrolidinoethyl amine. The F 1534 precipitates as it is formed. Purification is effected by treatment with an excess of bicarbonate to form the base of 1534, which is extracted by methylene chloride, and then rehydrochlorided by an ethanolic solution of hydrochloric acid.

The yield of crude product is 85% and of pure product 70%.

Developed Formula

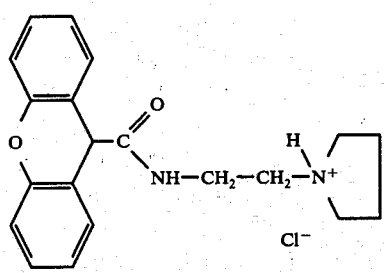

Empirical formula: $C_{20}H_{22}ClN_2O_2$
Molecular weight: 357.9
Melting point: 195° C.
White crystals Plate chromatography: support: silica gel solvent: BuOH/AcOH/H$_2$O 6/2/2 development: ultraviolet lamp and iodine vapors Rf: 0.65

Infrared spectrography: $\nu_{NH}$ 3230 and 3200 cm$^{-1}$ $\nu_{C=O}$ sintered to 1645 cm$^{-1}$ Solubility characteristics: very soluble in water. 10% soluble in ethanol and propylene glycol.

EXAMPLE 3

Synthesis of N(2'-pyrrolidino-ethyl)-α-phenyl-α-ethyl acetamide hydrochloride (F 1419)

To a solution of 1 mol of α-phenyl-α-ethyl acetyl chloride in 2 liters of benzene add, with agitation, a benzene solution of 1 mol of 2-pyrrolidino-ethyl amine. The hydrochloric acid formed during condensation attaches itself to the pyrrolidine group and the expected derivative crystallizes out in the reaction medium.

In order to favor the precipitation, ether may be added.

The yield of the reaction is quantitative for product of the formula:

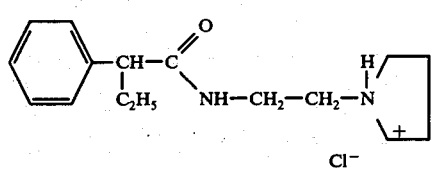

Empirical formula: $C_{16}H_{25}ClN_2O$
Molecular weight: 296.8
White crystals, slightly hygroscopic
Melting point: 160° C.

Plate chromatography: support: silica gel Merck G 254 solvent: butanol/acetic acid/water 6/2/2 development: untraviolet lamp or iodine vapor Rf: 0.44

Infrared spectrography: absorption band at 1645 cm$^{-1}$ of the C=O amide. Solubility characteristics: very soluble in water, insoluble in ether. 15% soluble in ethanol, 25% in propylene glycol and 7% in N-methyl pyrrolidone.

EXAMPLE 4

N(2'-pyrrolidino-ethyl)-10-phenothiazine carboxamide hydrochloride (F 1461)

To a suspension of 1 mol of 10-chlorocarbonyl-phenothiazine in 2 liters of acetone there is slowly added a solution of 1 mol of 2'-pyrrolidino-ethyl amine in acetone. After several hours at room temperature, the crystalline suspension is filtered, the crystals are treated with an aqueous solution of sodium bicarbonate, followed by extraction with methylene chloride; the organic phase is then distilled; the residue is taken up in an ethanolic solution of hydrochloric acid. The F 1461 precipitates upon the addition of ether.

The yield is about 70% of a derivative of the formula:

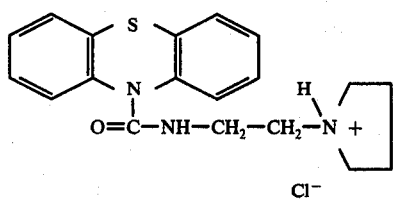

Empirical formula: $C_{19}H_{22}ClN_3OS$
White crystals
Melting point: 207° C.

Plate chromatography: support: silica gel solvent: butanol/acetic acid/water 6/2/2 development: ultraviolet lamp Rf: 0.55

Infrared spectrography: absorption bands: $\nu_{NH}$ to 3480 cm$^{-1}$ and $\nu_{C=O}$ to 1660 cm$^{-1}$. Solubility characteristics: 10% soluble in water, ethanol, propylene glycol and N-methyl pyrrolidone.

EXAMPLE 5

N(2′-pyrrolidino-ethyl)-α,α-diphenyl acetamide hydrochloride (F 1459)

Into a solution of 1 mol of diphenyl acetyl chloride in acetone there is gradually introduced with agitation 1 mol of pyrrolidino-ethyl amine in acetone solution. After 8 hours at room temperature, the acetone is distilled to dryness.

The residual oil is treated with an aqueous bicarbonate solution and extracted with chloroform; the organic phase is distilled to dryness, and the residue is taken up in an ethanolic solution of hydrochloric acid. The yield is 60% of a derivative of the formula:

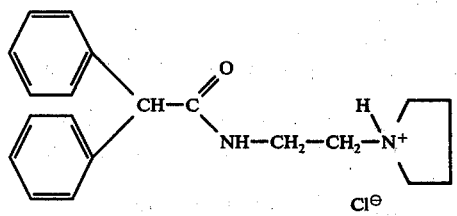

Empirical formula: $C_{20}H_{25}ClN_2O$
Molecular weight: 344.9
White crystals
Melting point: 179° C.

Plate chromatography: support: silica gel solvent: BuOH/AcOH/H$_2$O 6/2/2 development: iodine vapors Rf: 0.51

Infrared spectrography: Absorption bands: $\delta_{NH}$ at 3240 and 3200 cm$^{-1}$ $\delta_{C=O}$ at 1675 cm$^{-1}$ Solubility characteristics: 25% soluble in water, 5% in ethanol, 3% in propylene glycol.

EXAMPLE 6

N(2′-pyrrolidino-ethyl)-α,α-diphenyl-α-chloroacetamide hydrochloride

An acetone solution of 1 mol of diphenyl-α-chloroacetyl chloride is treated at 0° C. with an acetone solution of pyrrolidinoethylamine.

The derivative of the formula:

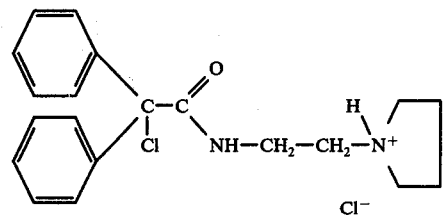

crystallizes out as it is formed.
Empirical formula: $C_{20}H_{24}Cl_2N_2O$
Molecular weight: 379.3
Melting point: 160° C.

EXAMPLE 7

N(2-pyrrolidino-ethyl)-α,α-diphenyl-α-ethoxy-acetamide hydrochloride (F 1460)

The derivative obtained in accordance with Example 6 is treated in suspension in absolute ethanol.

After refluxing for 4 hours and concentration under vacuum, the F 1460 precipitates upon the addition of ispropyl ether.

For purification it is possible to dehydrochlorinate by reaction of an aqueous bicarbonate solution and then after extraction with chloroform, distillation and treatment with an ethanolic solution of hydrochloric acid; the purified derivative is recovered with a yield of 80%.

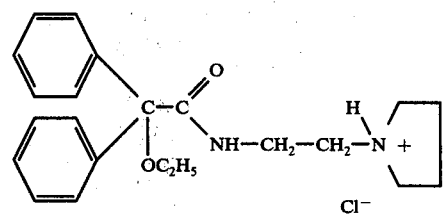

Empirical formula: $C_{22}H_{29}ClN_2O_2$
Molecular weight: 389
White crystals
Instantaneous melting point: 130° C.

Plate chromatography: support: silica gel solvent: BuOH/AcOH/H$_2$O 6/2/2 development: iodine vapors Rf: 0.63

Solubility characteristics: 1% soluble in water, 4% in ethanol, insoluble in ether.

EXAMPLE 8

N(2′-pyrrolidino-ethyl)-2-allyloxy-5-bromo-3-methyl benzamide hydrochloride (F 1479)

By treating the acid chloride of the formula:

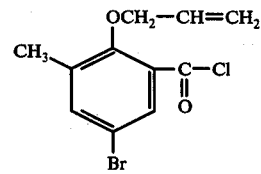

with a solution of pyrrolidino-ethyl amine and, after customary treatment there is recovered, in quantitative yield, the derivative of the formula:

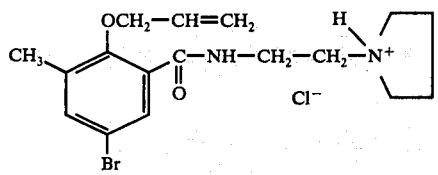

Empirical formula: $C_{17}H_{24}ClBrN_2O_2$
Molecular weight: 403.7
White crystals
Melting point: 118° C.
Plate chromatography: support: silica gel solvent: butanol/acetic acid/water 6/2/2 development: ultraviolet lamp and iodine vapors Rf: 0.62
Solubility characteristics: very soluble in water.

EXAMPLE 9
N(2'-pyrrolidino-ethyl)-5-bromo-3-methyl-salicylamide hydrochloride Methyl-5-bromo-3-methyl salicylate, suspended in pyrrolidino-ethylamine, is treated at 90° C. for 4 hours. The methanol is distilled off as it is formed. The reaction mixture is then treated with 6N hydrochloric acid, and the initial methyl ester is extracted with ether; the aqueous phase is treated with ammonia, extracted with ether, washed, dried, evaporated to dryness, and then hydrochlorided by an ethanolic solution of hydrochloric acid, precipitated with ether, filtered, and washed.

The derivative of the formula:

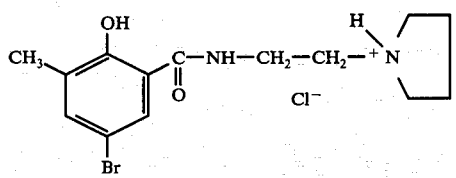

is recovered in a yield of 80%.
Empirical formula: $C_{14}H_{20}BrClN_2O_2$
Molecular weight: 363.7
White crystals
Melting point: 184° C.
Plate chromatography: support: silica gel solvent: butanol/acetic acid/water 6/2/2 development: ultraviolet lamp and iodine vapors
Rf: 0.75
Solubility characteristics: very soluble in water, 3% soluble in ethanol, 7% in propylene glycol, insoluble in ether.

The following derivatives were also obtained by Methods 1 and 2.

EXAMPLE 10
N(2'-pyrrolidino-ethyl)-α,α-diphenyl-hydroxy-acetamide hydrochloride (F 1535)

Developed formula:

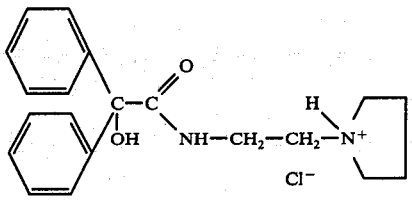

Empirical formula: $C_{20}H_{25}ClN_2O_2$
Molecular weight: 360.9
White crystals
Melting point: 209° C.
Plate chromatography: support: silica gel Merck G 254 solvent: BuOH/AcOH/H$_2$O 6/2/2 development: UV and iodine Rf: 0.64
Infrared spectrography: $\delta_{NH}$ and $\delta_{OH}$ wide absorption band at 3250 cm$^{-1}$ $\delta_{C=O}$ at 1665 cm$^{-1}$. Solubility characteristics: very soluble in water.

EXAMPLE 11
N(2'-pyrrolidino-ethyl)phenyl piperidino-acetamide (F 1533)

Developed Formula:

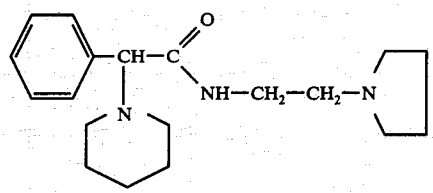

Empirical formula: $C_{19}H_{29}N_3O$
Molecular weight: 315.5
Beige crystals
Melting point: 80° C.
Infrared spectrography: $_{NH}$ at 3350 cm$^{-1}$ and $_{C=O}$ at 1665 cm$^{-1}$
Plate chromatography: support: Merck silica gel solvent: BuOH/AcOH/H$_2$O 6/2/2 development: UV and iodine Rf: 0.13
Solubility characteristics: insoluble in water. Very soluble in ethanol.

EXAMPLE 12
N(2'-pyrrolidino-ethyl)-2-carboxy-benzamide (F 1537)

This derivative is obtained from phthalic anhydride in solution in acetone treated with 2-amino-ethyl-pyrrolidine. The F 1537 crystallizes out in the form of a monohydrate.

Developed formula:

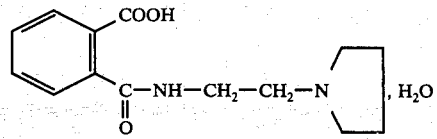

Empirical formula: $C_{14}H_{20}N_2O_4$
Molecular weight: 280.3
Crystals of impure white color
Instantaneous melting point: 130° C.

Infrared spectrography: $\nu_{NH}$ at 3240 cm$^{-1}$ $\nu_{C=O}$ (acid) low at 1710 cm$^{-1}$ $\nu_{C=O}$ (amide) at 1645 cm$^{-1}$ $\nu_{C=O}$ (internal salt COO$^-$) intense at 1550 and 1600 cm$^{-1}$.

Plate chromatography: support: Merck silica gel solvent: methylethylketone/N-propanol/EtOH/NH$_4$OH 34% 90/9/36/64 development: ultraviolet lamp or iodine vapors Rf: 0.69

Solubility characteristics: very soluble in water, ethanol and propylene glycol.

EXAMPLE 13

N(2'-pyrrolidino-ethyl)cinnamide, HCl (F 1542)

Developed formula:

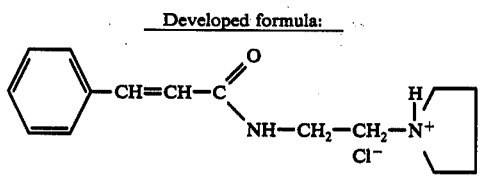

Empirical formula: C$_{15}$H$_{21}$ClN$_2$O
Molecular weight: 280.8
White crystals
Melting point: 202° C.
Infrared spectrography: $\nu_{N-H}$ 3260 cm$^{-1}$ $\nu_{C=O}$ (amide) 1670 cm$^{-1}$ $\nu_{C=C}$ (ethylene) 1630 cm$^{-1}$ Plate chromatography: support: Merck silica gel solvent: BuOH/AcOH/H$_2$O 6/2/2 development: ultraviolet lamp or iodine vapors Rf: 0.81

Solubility characteristics: very soluble in water, ethanol and propylene glycol.

EXAMPLE 14

N(2'-pyrrolidino-ethyl)-3-coumarin-carboxamide hydrochloride

Developed formula:

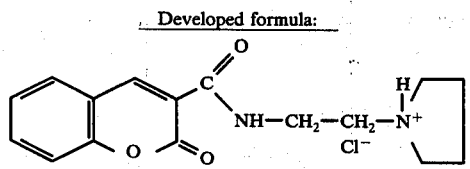

Empirical formula: C$_{16}$H$_{19}$ClN$_2$O$_3$
Molecular weight: 322.8
Beige crystals
Melting point: 220° C.
Infrared spectrography: $\nu_{NH}$ at 3330 cm$^{-1}$ $\nu_{C=O}$ (lactone) 1700 cm$^{-1}$ $\nu_{C=O}$ amide 1660 cm$^{-1}$ $\nu_{C=C}$ at 1610 cm$^{-1}$ Plate chromatography: support: Merck silica gel solvent: BuOH/AcOH/H$_2$O 6/2/2 development: ultraviolet lamp or iodine vapors Rf: 0.53

Solubility characteristics: very soluble in water. 4% soluble in ethanol, 7% in propylene glycol.

EXAMPLE 15

N(2'-pyrrolidino-ethyl)-4-chloro-phenoxy-isobutyramide hydrochloride (F 1541)

Developed formula:

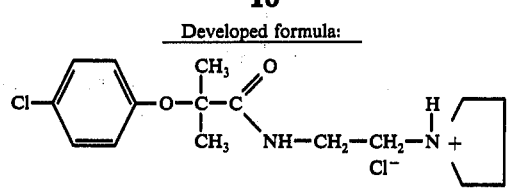

Empirical formula: C$_{16}$H$_{24}$Cl$_2$N$_2$O$_2$
Molecular weight: 347.3
White crystals
Melting point: 140°
Infrared spectrography: salification bands 2500 to 3500 cm$^{-1}$ $\nu_{N-H}$ 3230 cm$^{-1}$ $\nu_{C=O}$ (amide) 1660 cm$^{-1}$ $\nu_{C=C}$ 1600 cm$^{-1}$ Plate chromatography: support: Merck silica gel solvent: BuOH/AcOH/H$_2$O 6/2/2 development: ultraviolet lamp or iodine vapors Rf: 0.57

Solubility characteristics: Soluble in water, ethanol, and propylene glycol.

EXAMPLE 16

N(2'-pyrrolidino-ethyl)phenoxy-isobutyramide hydrochloride (F 1540)

Developed formula:

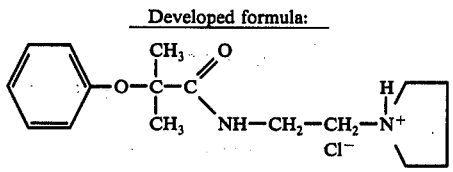

Empirical formula: C$_{16}$H$_{25}$ClN$_2$O$_2$
Molecular weight: 312.8
White crystals
Melting point: 94°
Infrared spectrography: salification bands 2500 to 3500 cm$^{-1}$ $\nu_{NH}$ at 3250 cm$^{-1}$ $\nu_{C=O}$ at 1660 cm$^{-1}$ $\nu_{C=C}$ at 1600 cm$^{-1}$.

Plate chromatography: support: Merck silica gel solvent: BuOH/AcOH/H$_2$O 6/2/2 development: UV and iodine Rf: 0.58

Solubility characteristics: soluble in water, ethanol and propylene glycol.

EXAMPLE 17

N(2'-pyrrolidino-ethyl)-4-chloro-phenoxy-acetamide hydrochloride (F 1539)

Developed formula:

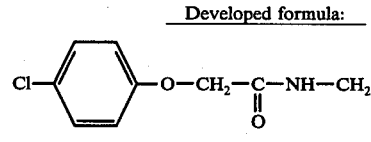

Empirical formula: C$_{14}$H$_{20}$Cl$_2$N$_2$O$_2$
Molecular weight: 319.2
White crystals
Double melting point: 95° and 144° C.
Infrared spectrography: salification bands at 2500 to 3500 cm$^{-1}$ $\nu_{NH}$ 3260 cm$^{-1}$ $\nu_{C=O}$ (amide) 1660 cm$^{-1}$ $\nu_{C=C}$ 1600 cm$^{-1}$ Plate chromatography: support: Merck silica gel solvent: BuOH/AcOH/H$_2$O 6/2/2 development: ultraviolet lamp or iodine vapors Rf.: 0.45

Solubility characteristics: soluble in water, ethanol, and propylene glycol.

EXAMPLE 18

N(2'-pyrrolidino-ethyl)-3-4-5-trimethoxy-benzamide hydrochloride (F 1538)

Developed formula:

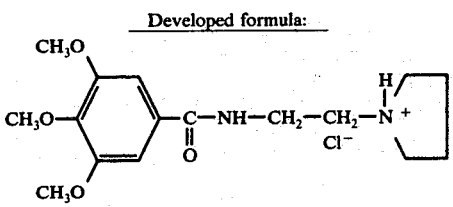

Empirical formula: $C_{16}H_{25}ClN_2O_4$
Molecular weight: 344.8
Beige crystals
Melting point: 158° C.

Infrared spectrography: Salification bands 2500 to 3550 cm$^{-1}$ $\nu_{NH}$ 3290 cm$^{-1}$ $\nu_{C=O}$ (amide) 1650 cm$^{-1}$ Plate chromatography: support: Merck silica gel solvent: BuOH/AcOH/H$_2$O 6/2/2 development: UV and iodine Rf: 0.5

Solubility characteristics: soluble in water, ethanol, and propylene glycol.

Obtaining of New Salts

The hydrochloride derivatives described in the above examples can be treated by the following techniques in order to obtain new therapeutically acceptable salts whose organoleptic properties, and more particularly flavor, are however improved.

Salification Experimental Record

Method A - transalification

The water insoluble salts are prepared by addition of an aqueous solution of one equivalent of the hydrochloride of the base to an aqueous solution of one equivalent of the sodium salt of the acid.

The salt is centrifuged, washed with water until disappearance of the chloride. Dry under vacuum to constant weight.

Method B - direct salification

The hydrochloride of the amine is treated with an aqueous solution of sodium bicarbonate and the base is extracted with chloroform. Dry. Filter. This solution is added to a solution or suspension of the acid in chloroform.

Dissolve. Concentrate the solution and crystallize the salt by addition of ether.

EXAMPLE 19 (illustrates Method A)

N(2-pyrrolidino-ethyl)-α,α-diphenyl-acetamide pamoate (F 1629)

A solution of 0.15 mol of N(2 -pyrrolidino-ethyl)diphenylacetamide hydrochloride in 2.5 liters of water is added to a solution of 0.075 mol of sodium salt of pamoic acid in 1 liter of water.

The precipitate obtained is centrifuged, washed with water until disappearance of the chloride and dried under vacuum to constant weight.

The yield of the product of the following formula is 95%.

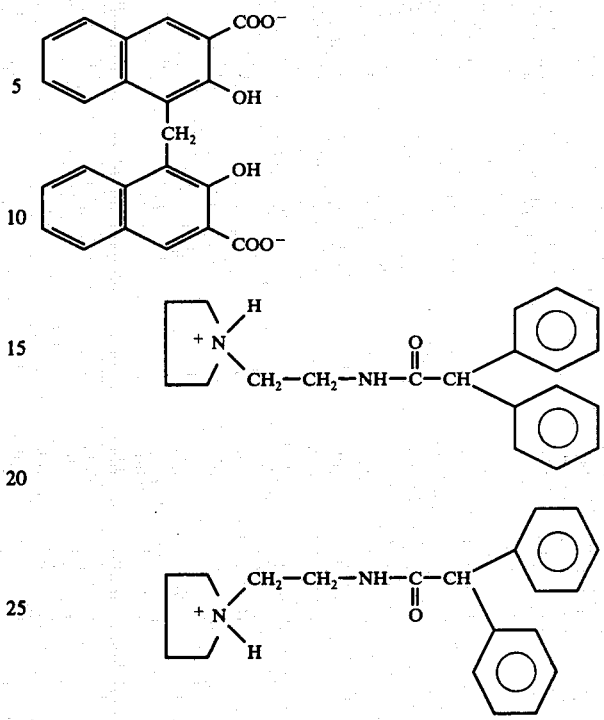

Empirical formula: $C_{63}H_{64}N_4O_8$
Molecular weight: 1005.23
Yellow crystals
Instantaneous melting point: 145°

Infrared spectrography: Salification band 2500 to 3500 cm$^{-1}$ $\nu_{C=O}$ (amide) 1645 cm$^{-1}$ $\nu_{C=O}$ (COO$^-$) 1565 cm$^{-1}$ Plate chromatography: support: silica gel solvent: Butanol/acetic acid/water 6/2/2 development: ultraviolet lamp or iodine vapors Rf: acid: 0.70 (UV - FeCl$_3$) base: 0.35 (UV)

Solubility characteristics: Insoluble in water and alcohol. Soluble in methyl pyrrolidone and dimethyl acetamide.

EXAMPLE 20 (Method A)

N(2-pyrrolidino-ethyl)-α,α-diphenyl-acetamide palmitate (F 1630)

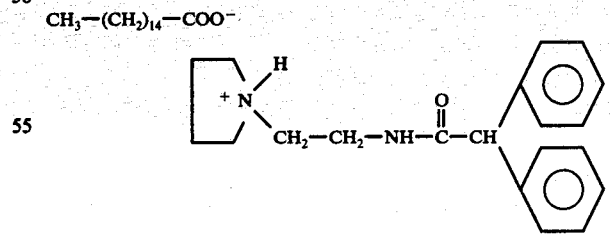

Empirical formula: $C_{36}H_{56}N_2O_3$
Molecular weight: 564.82
White crystals
Instantaneous melting point: 55°

Infrared spectrography: salification bands 2500 to 3500 cm$^{-1}$ $\nu_{NH}$ 3270 cm$^{-1}$ $\nu_{C=O}$ (amide) 1645 cm$^{-1}$ Plate chromatography: support: silica gel solvent: butanol/acetic acid/water 6/2/2 development: ultraviolet lamp or iodine vapors Rf: base: 0.35 (UV) acid: 0.85 (rhodamine + UV)

Solubility characteristics: Insoluble in water. Poorly soluble in alcohol, dimethyl acetamide, methyl pyrrolidone, and propylene glycol.

The new derivatives obtained in the foregoing manner, which are bases, can be converted into addition salts with acids, which form part of the invention. The addition salts can be obtained by the reaction of the new derivatives with acids in suitable solvents such, for example, as shown by the examples. As acids used for the formation of these addition salts there may be mentioned, in the mineral series: hydrochloric, hydrobromic, methanesulphonic, sulphuric and phosphoric acid; in the organic series: acetic, propionic, maleic, fumaric, tartaric, citric, oxalic, benzoic acid, to name a few.

The invention accordingly also relates to the salts with organic or inorganic acids, especially lipophilic acids, e.g., fatty acids having 14 to 22 carbon atoms, inclusive, which are linear or branched, saturated or unsaturated, including palmitic, linoleic, linolenic, and oleic acids, and the like, as well as of the naphthoic type, especially pamoic acid, in addition to the usual organic and inorganic acids of the type already mentioned.

Moreover, in addition to the substituents $R_1$ and $R_2$ as specifically illustrated by the Examples for Formula II, the same and/or additional substituents as specifically shown for $R_1$ and $R_2$ may be present, and $R_1$ may be present in a different ring position, e.g., in a different position of the benzene ring with respect to the $R_2$ and X substituents present therein. X may, for example, be fluoro, bromo, chloro, or iodo. Either or both of $R_1$ and $R_2$ may be, for example, methyl, ethyl, propyl, amyl, methoxy, ethoxy, propoxy, amyloxy, propenyloxy, butenyloxy, propynyloxy, butynyloxy, hydroxyethoxy, hydroxypropyloxy, hydroxybutyloxy, or hydroxyamyloxy or the like, "lower" in each case meaning a maximum of (5) carbon atoms in such group. The nature and location of these substituents depends only upon the selected starting compound employed in the preparation thereof, as will be apparent and fully within the ability of one skilled in the art, as will selection and preparation of the desired acid addition salt of such compound in any particular case.

EXPERIMENTAL

The high order of activity of the active agents of the present invention has been evidenced by tests in lower animals and representative of these are reported herein.

A - Toxicology

The chemical compounds previously described were subjected to toxicity tests.

The acute toxicity, determined by the 50% lethal dose (DL 50), is reported in the following table.

It is determined on mice, the products being administered orally, intraperitoneally, and intraveneously in isotonic aqueous solution.

| Compounds | DL 50 (mg/kg) | | |
|---|---|---|---|
| | oral | intraperitoneal | intravenous |
| F 1419 | 660 | 200 | 76 |
| F 1459 | 562 | 178 | 48 |
| F 1460 | 750 | 178 | 40 |
| F 1461 | 560 | 178 | 26 |

| Compounds | DL 50 (en mg/kg) | |
|---|---|---|
| | oral | intraperitoneal |
| F 1532 | 178 | 75 |
| F 1533 | 750 | 178 |
| F 1534 | 750 | 178 |
| F 1535 | 562 | 237 |
| F 1536 | 1000 | 300 |
| F 1537 | 1000 | 500 |
| F 1538 | 562 | 300 |
| F 1539 | 1000 | 178 |
| F 1540 | 1000 | 237 |
| F 1541 | 562 | 178 |
| F 1542 | 1000 | 178 |
| F 1543 | 1000 | 178 |
| F 1629 | 2000 | 750 |
| F 1630 | 1500 | 500 |

B - Pharmacology

The pharmacological experiments to which these new compounds were subjected disclosed interesting antitussive properties upon using the citric acid aerosol method on guinea pigs.

The animals were subjected to a 20% citric acid aerosol for 15 minutes.

The coughs were recorded by a microphone.

The products were administered intraperitoneally 20 minutes before the exposure to the aerosol.

The results are summarized in the following table.

| Lots | Citric Acid Aerosol Method (on guinea pigs) | |
|---|---|---|
| | dose in mg/kp i.p. | % reduction of no. of coughs in 15 minutes |
| Controls | — | 22 |
| | | 20 |
| F 1532 | 25 | −15% |
| F 1533 | 50 | −7% |
| F 1534 | 50 | −63% |
| F 1535 | 50 | −43% |
| F 1536 | 50 | 0 |
| F 1537 | 50 | −8% |
| F 1538 | 50 | −1% |
| F 1539 | 50 | −18,5% |
| F 1540 | 50 | −22% |
| F 1541 | 50 | −26% |
| F 1542 | 50 | −19,5% |
| F 1543 | 50 | −19% |
| F 1630 | 50 | −60% |
| F 1629 | 50 | −60% |
| F 1419 | 50 | −35% |
| F 1459 | 50 | −65% |
| F 1460 | 50 | −20% |
| F 1461 | 50 | −56% |

Some derivatives were also tested orally. By way of example, we cite a few results as compared with the citric acid aerosol.

| Compounds | orally doses in mg/kg | % decrease in no. coughs in 15 mins. |
|---|---|---|
| F 1419 | 100 | −40 |
| | 50 | −22 |
| F 1459 | 50 | −31 |
| F 1461 | 50 | −12 |
| | 100 | −25 |
| F 1629 | 100 | −50 |
| | 50 | −30 |

A second method using a different type of stimulation of coughs made it possible to note, as compared with codeine, the antitussive properties of the main components claimed.

The technique employed is derived from Takagi's technique, and consists in causing coughing by mechanical stimulation of the tracheal bifurcation in the unanesthetized guinea pig.

The cough is evaluated by the research worker in accordance with the following scale:
1: heavy cough
0.5: light cough
0: no cough The products are administered intraperitoneally and the stimulation is effected 10 and 20 minutes after the injection.

The results are set forth in the following table:

| Lots | weight | parameters | Takagi's Technique Cough rating before treatment | | after treatment | |
|---|---|---|---|---|---|---|
| | | | to | to + 5 mn | t + 10 mn | t + 20 mn |
| CONTROLS | 310 | no. of animals | 12 | 12 | 12 | 12 |
| | | m | 1,0 | 0,96 | 0,83 | 0,83 |
| | | s2 | 0 | 0,020 | 0,060 | 0,106 |
| | | Em | 0 | 0,03 | 0,07 | 0,09 |
| F 1459 | 330 | no. of animals | 12 | 12 | 12 | 12 |
| 50 mg/kg | | m | 1,0 | 0,96 | 0,67 | 0,33 |
| | | s2 | 0 | 0,020 | 0,106 | 0,151 |
| | | Em | 0 | 0,03 | 0,09 | 0,11 |
| | | % variation | | | −32% S. | −66% H.S. |
| F 1461 | 310 | no. of animals | 12 | 12 | 12 | 12 |
| 50 mg/kg | | m | 0,87 | 0,79 | 0,54 | 0,37 |
| | | s2 | 0,051 | 0,067 | 0,248 | 0,233 |
| | | Em | 0,06 | 0,07 | 0,14 | 0,14 |
| | | % variation | | | −35% N.S. | −55% S. |
| Reference | 310 | no. of animals | 12 | 12 | 12 | 12 |
| CODEINE | | m | 0,96 | 0,96 | 0,75 | 0,67 |
| 50 mg/kg | | s2 | 0,020 | 0,020 | 0,113 | 0,151 |
| | | Em | 0,03 | 0,03 | 0,03 | 0,11 |
| | | % variation | | | −22% N.S. | −30% S. | m = average of the ratings;
S2 = variance;
Em = difference from mean
S.: result significant
N.S.: result not significant
H.S.: result highly significant The determination of fungistatic bacteriostatic properties was carried out by two methods on four strains:

Diffusion Method

The microorganisms are introduced into nutrient agar. On the surface, paper disks soaked with the products to be tested are deposited, after 18 hours incubation. The diameter of the growth inhibition zones is measured.

Measurement of the Minimum Inhibitory Concentration (M.I.C.)

Halved serial dilutions are formed in a hemoylsis tube, in each case to a volume of 1 ml; each dilution is inoculated with $10^6$ micro-organisms per ml. After 48 hours in the oven, the minimum inhibitory concentration is determined. A subculture of the negative tubes (bacteriostatic), makes it possible to note the bactericidal concentration. A significant action with respect to *Staphylococcus aureus* and *Escherichia coli* was obtained with the products F 1459, F 1532, F 1533, F 1534 with MICs of the order of 625μg; a more moderate but significant effect was obtained with *Pseudomonas aeruginosa* and *Candida albicans*. These products are accordingly not major antiseptics, but their bactericidal action is real and significant at concentrations of 1 g percent.

Additional Properties

Furthermore, certain derivatives showed a high order of local anesthesia activity comparable to that of procaine; these were F 1534, F 1535 and F 1541.

The antalgic properties with respect to a decrease in contortions caused by phenyl benzoquinone, as measured in mice, are very clear from the 150 mg/kg by mouth in the case of F 1534 (40% decrease), F 1539 (75% decrease), and F 1541 (60% decrease).

Compositions and Method of Treating

The foregoing properties taken together, and the low toxicity of these compounds, confirmed by a subacute toxicity study for six weeks on two species of animals, namely rats and dogs, make it possible at the present time to test these derivatives clinically for their use in respiratory therapy and in the treatment of certain pains. The new derivatives thus show antitussive and, in certain cases also local anesthesia, properties sufficient to permit their use in therapy for the treatment of laryngotracheitis, stubborn tracheitis, nervous cough, and smoker's cough. These therapy treatments were carried out by means of suitable pharmaceutical forms, using either the product in its initial free basic form or in the form of a therapeutically acceptable salt. The novel compounds are preferably used in the form of their pharmaceutically-acceptable acid addition salts, e.g., their hydrochlorides, hydrobromides, or the like. The salt form is also the best form for pharmaceutical formulations. Innumerable other pharmaceutically-acceptable acid addition salts can be prepared from the hydrochlorides via the free bases in conventional manner. For oral use, the compounds are usually administered as tablets, solutions, or suspensions, in which they are present together with usual pharmaceutical carriers, excipients, binders, and the like. For example, tablets may be prepared conventionally by compounding one of the new compounds, preferably in the form of an acid addition salt thereof, with customary carriers and adjuvants, e.g., talc, magnesium stearate, starch, lactose, gelatin, gums, and the like. In their most advantageous form, then, the compositions of the present invention will contain a non-toxic pharmaceutical carrier in addition to the active ingredient. Exemplary carriers are:

Solids: lactose, magnesium stearate, calcium stearate, starch, terra alba, dicalcium phosphate, sucrose, talc, stearate acid, gelatin, agar, pectin, acacia, or other usual excipient;

Liquids: peanut oil, sesame oil, oliver oil, water, elixir, or other usual excipient. The active agents of the invention can be most conveniently administered in such compositions containing about 0.01 to 67 percent, preferably 0.04 to 12.15 percent, by weight of the active ingredient. Such formulations are representatively illustrated in U.S. Pat. No. 3,402,244.

A wide variety of pharmaceutical forms suitable for many modes of administration and dosages may be employed. For oral administration, the active ingredient and pharmaceutical carrier may, for example, take the form of a granule, pill, tablet, lozenge, elixir, syrup, or other liquid suspension or emulsion; and for rectal administration, a suppository.

The method of using the compounds of the present invention comprises internally administering a compound of the invention, usually in the form of a non-toxic, pharmacologically-acceptable acid addition salt, and preferably admixed with a pharmaceutical carrier, for example, in the form of any of the above-mentioned compositions, or filled into a capsule, to alleviate one or more of the foregoing enumerated conditions and symptoms in a living animal body, whether human or domestic animal, for example, the aforementioned cough. The compounds, and especially their non-toxic salts, may be advantageously employed in amounts of about 1 to 50 milligrams per unit dose, preferably about 2.5 to 25 milligrams per unit dose, preferably and usually in admixture with the conventional carrier. The unit dose is preferably given a suitable number of times daily so that the daily dose may vary from about 5 to about 100 milligrams. However, the compounds are subject to usual variations in optimum daily and unit dosages, due to patient body weight, condition, and ancillary factors, and the invention therefore should not be limited by the exact ranges stated. The exact dosage, both unit and daily, will of course have to be determined according to established veterinary and medical principles. The doses for administration usually vary for oral and rectal administration from about 5 to about 100 mg over a period of 24 hours, and the active substances are generally administered orally in the form of capsules, tablets of normal or delayed action, syrups and drops, and rectally in the form of suppositories or rectal capsules.

The active principles of the present invention may be used alone or together with or in combination with other or supplementary active principles for the particular treatment involved, such as antihistamines, expectorants and bronchic fluidizers, antibiotics, corticoids, vitamins, analgesics, anticholinergics, sedatives, stimulants, buffering agents, antacids, or the like. By way of illustration, but not of limitation, we cite a few representative galenical preparations, which are representative for all of the pharmacologically active compounds of the invention, but which have been particularly designed to embody as active ingredient the particular compounds embodied therein, especially in the form of a pharmaceutically acceptable salt thereof:

(a) tablets 50 mg of F 1535
excipient q.s.p.

(b) syrup

F 1639 — 200 mg
Na guiacol sulfonate — 600 mg
terpene hydrate — 1 g
excipient q.s.p.

(c) suppositories

F 1534 — 10 mg
Promethazine — 30 mg excipient g.s.p.

(d) long-action tablets

F 1629 — 50 mg
excipient q.s.p.

(e) syrup

F 1419
Vitamin C
antibiotic (f) suppository

F 1459 — 10 mg

General

The free bases of the invention may generally by extracted with a suitable organic solvent, e.g., ether, methyl-butyl ketone, or the like, if desired. Salts with pharmaceutically acceptable acids, e.g., hydrochloric, hydrobromic, fumaric, citric, maleic, tartaric, or lactic, or the like, may also be precipitated with acid from a dried solution of the free base in a conventional manner and recrystallized, if desired (See Example 7), instead of directly, as also shown herein. One acid salt, even if not pharmaceutically acceptable, is still useful, since it can readily be converted to another salt which is pharmaceutically acceptable in known manner, e.g., by alkalization and then acidification with a different acid, if desired.

Where the foregoing examples produce a compound having a methyl or other lower-alkyl group, it is to be understood that compounds containing other lower-alkyl groups of straight or branched nature and containing up to five carbon atoms, inclusive, such as methyl, ethyl, propyl, isopropyl, butyl, sec.-butyl, t.-butyl, amyl and isoamyl, are prepared in the same manner by substitution in the process of the appropriate different lower-alkyl starting material. Likewise, where chloro or other halogen atom is present, although chlorine is preferred, further halogen compounds including iodo, bromo, chloro, and fluoro compounds are prepared starting from the appropriate halogenated starting material. Similarly, where methoxy or other lower-alkoxy group is present, compounds having other lower-alkoxy groups containing various lower-alkyl groups having up to five carbon atoms inclusive are prepared in the same manner from the appropriate different lower-alkoxy starting material. In the same manner, ortho and meta products are produced instead of the para by utilizing the selected ortho or meta substituted starting material and vice versa. Similarly, other molecular changes within the scope of the invention are readily made.

It is to be understood that the invention is not to be limited to the exact details of operation or exact compounds, compositions, or procedures shown and described, as obvious modifications and equivalents will be apparent to one skilled in the art, and the invention is therefore to be limited only by the scope of the appended claims.

We claim:

1. Method for the treatment of a patient suffering from cough, comprising administering to the patient a compound selected from the group consisting of (a) a pyrrolidinoethylamine amide of the formula:

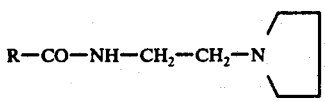

wherein

is an acyl radical of a phenylacetic, α-phenyl-α-loweralkyl (1-5 carbon atoms) acetic, diphenylacetic, benzilic, diphenyl-α-chloroacetic, and α-lower-alkoxy-α,α-diphenylacetic, and (b) a pharmaceutically acceptable acid addition salt thereof, in an amount effective for the alleviation of said condition.

2. Method of claim 1 employing a pharmaceutically acceptable acid addition salt of a basic pyrrolidinoethylamine amide.

3. Method of claim 1 employing a hydrochloride of a basic pyrrolidinoethylamine amide.

4. Method of claim 1 employing a pharmaceutically acceptable acid addition salt wherein the acid is a lipophilic acid, selected from the group consisting of fatty acids of 14 to 22 carbon atoms, inclusive, and pamoic acid.

5. Method of claim 1 employing a compound wherein R is diphenyl-CH-.

6. Method of claim 1 employing a compound wherein R is diphenyl-C(OH)-.

7. Method of claim 1 employing a compound wherein R is phenyl-CH($C_2H_5$)-.

8. Method of claim 1 employing a compound wherein R is diphenyl-C(B)-, wherein B is hydrogen or hydroxy.

9. Method of claim 5 employing a pharmaceutically acceptable acid addition salt wherein the acid is a lipophilic acid, selected from the group consisting of fatty acids of 14 to 22 carbon atoms, inclusive, and pamoic acid.

10. Method of claim 1 employing a compound which is N(2'-pyrrolidinoethyl)-α-phenyl-α-ethylacetamide acid addition salt.

11. Method of claim 1 employing a compound which is N(2'-pyrrolidinoethyl)-α,α-diphenylacetamide acid addition salt.

12. Method of claim 1 employing a compound which is N(2'-pyrrolidinoethyl)-α,α-diphenyl-α-chloroacetamide acid addition salt.

13. Method of claim 1 employing a compound which is N(2'-pyrrolidinoethyl)-α,α-diphenyl-α-ethoxyacetamide acid addition salt.

14. Method of claim 1 employing a compound which is N(2'-pyrrolidinoethyl)diphenylhydroxyacetamide acid addition salt.

15. Method of claim 1 employing a compound which is N(2'-pyrrolidinoethyl)-α,α-diphenylacetamide pamoate.

16. Method of claim 1 employing a compound which is N(2'-pyrrolidinoethyl)-α,α-diphenylacetamide palmitate.

17. Method of claim 1 employing a compound which is N(2'-pyrrolidinoethyl)-α,-α-diphenylacetamide hydrochloride.

* * * * *

UNITED STATES PATENT AND TRADEMARK OFFICE
CERTIFICATE OF CORRECTION

PATENT NO. : 4,122,199
DATED : October 24, 1978
INVENTOR(S) : Cousse et al.

It is certified that error appears in the above-identified patent and that said Letters Patent are hereby corrected as shown below:

[57] ABSTRACT, first line below second formula; "60" should read --α--

[57] ABSTRACT; "α-(1 to 5 C atoms) acetic, (1 to 5 C atoms) diphenylacetic," should read --α-lower-alkyl(1 to 5 C atoms) acetic, diphenylacetic,--

Col. 2, lines 13 & 14; "pheny-l" should read --phenyl--
Col. 2, line 46; "insance" should read --instance--
Col. 2, line 62; "fluoroene" should read --fluorene--
Col. 4, line 43; "untraviolet" should read --ultraviolet--
Col. 6, line 24; "ispropyl" should read --isopropyl--
Col. 9, line 40; "hydrochloride" should read --hydrochloride (F 1543)--
Col. 17, line 67; "F 1639" should read --F 1629--
Col. 18, line 21; "by" should read --be--

Signed and Sealed this

Twentieth Day of November 1979

[SEAL]

Attest:

RUTH C. MASON
Attesting Officer

LUTRELLE F. PARKER
Acting Commissioner of Patents and Trademarks